(12) United States Patent
Zhan et al.

(10) Patent No.: US 11,123,341 B2
(45) Date of Patent: Sep. 21, 2021

(54) BUTYRYLCHOLINESTERASE INHIBITORS FOR TREATMENT OF OPIOID USE DISORDER

(71) Applicant: University of Kentucky Research Foundation, Lexington, KY (US)

(72) Inventors: Chang-Guo Zhan, Lexington, KY (US); Fang Zheng, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 16/883,291

(22) Filed: May 26, 2020

(65) Prior Publication Data

US 2020/0368224 A1    Nov. 26, 2020

Related U.S. Application Data

(60) Provisional application No. 62/852,724, filed on May 24, 2019.

(51) Int. Cl.
| | | |
|---|---|---|
| *A61K 31/485* | (2006.01) | |
| *A61K 31/5415* | (2006.01) | |
| *A61P 25/36* | (2006.01) | |

(52) U.S. Cl.
CPC ............ *A61K 31/485* (2013.01); *A61P 25/36* (2018.01)

(58) Field of Classification Search
CPC .... A61K 31/5415; A61K 31/485; A61P 25/36
USPC .................................. 514/226.2, 224.5, 282
See application file for complete search history.

(56) References Cited

PUBLICATIONS

Selley, D. E. et al. mu-Opioid receptor-mediated G-protein activation by heroin metabolites: evidence for greater efficacy of 6-monoacetylmorphine compared with morphine. Biochem. Pharmacol. 62, 447-455 (2001).
Salmon, A. Y., Goren, Z, Avissar, Y. & Soreq, H. Human erythrocyte but not brain acetylcholinesterase hydrolyses heroin to morphine. Clinical and Experimental Pharmacology and Physiology 26, 596-600 (1999).
Atack, O. A., Vu, Q.-S., Soncrant, T. T., Brossi, A. & Rapoport, S. I. Comparative Inhibitory Effects of Various Physostigmine Analogs against Acetyl- and Butyryicholinesterases. J. Pharm. Exp. Therap. 249, 194-202 (1989).
Giacobini, Ezio. Selective Inhibitors of Butyrylcholinesterase: A valid alternative for therapy of Alzheimer's Disease? Drug Aging. 18(12) 891-898 (2001).

*Primary Examiner* — Charanjit Aulakh
(74) *Attorney, Agent, or Firm* — Stites & Harbison PLLC; Mandy Wilson Decker; Gary N. Stewart

(57) ABSTRACT

A method of treating opioid use disorder involves administering a selective butyrylcholinesterase (BChE) inhibitor.

20 Claims, 4 Drawing Sheets

BUTYRYLCHOLINESTERASE INHIBITORS FOR TREATMENT OF OPIOID USE DISORDER

RELATED APPLICATIONS

This application claims priority from U.S. Provisional Application Ser. No. 62/852,724 filed May 24, 2019, the entire disclosure of which is incorporated herein by this reference.

GOVERNMENT INTEREST

This invention was made with government support under grant numbers UH2/UH3 DA041115, R01 DA035552, R01 DA032910, R01 DA013930, and R01 DA025100 awarded by the National Institutes of Health. The government has certain rights in the invention.

TECHNICAL FIELD

The presently-disclosed subject matter relates to butyrylcholinesterase inhibitors and methods for treating opioid use disorder (OUD), including opioid abuse and opioid toxicity, by administration of a butyrylcholinesterase inhibitor.

INTRODUCTION

Opioid abuse is known as a national crisis in America, due to the rapidly increasing overdose deaths. From 2001 to 2014, heroin overdose deaths nationwide increased 594 percent and continued to dramatically increase since 2014, according to the Centers for Disease Control (www.cdc.gov/drugoverdose/epidemic/index.html), and "heroin is scarring the next generation".[1]

The connection between heroin abuse and prescription opioid abuse is related to the actual availability, in addition to the common brain protein target (μ-opiate receptors), of these opioid drugs. In fact, "80% of recent heroin initiates reported that they began their opioid use through the nonmedical use of prescription opioid medications".[2] The prevalence of prescription opioid abuse is similar among men and women. Those who abuse the prescription drugs most often obtain them from friends and family either through sharing or theft. When they are no longer able to get prescription opioid drugs, they start to use illegal opioid heroin, because heroin is easy to obtain on the street and even online. In addition, heroin has become much cheaper than any other drug of abuse, e.g. $10-$20 for a typical single dose (0.1 g) of heroin purchased on the street.[2]

Due to the connection between heroin abuse and prescription opioid abuse, further enhancing law enforcement through improving existing prescription drug monitoring programs[3] might effectively reduce the prescription opioid abuse. On the flip side, the reduced prescription opioid abuse could lead to increase of the heroin abuse. As a result, the overall opioid overdose deaths might not really decrease. For example, study showed prescription drug abuse declining in Kentucky,[4] due to the strict Kentucky All Schedule Prescription Electronic Reporting Program (KASPER). Unfortunately, the heroin overdose has dramatically increased,[4] and the total number of drug overdose deaths actually went up in Kentucky.[2,5] Accordingly, further enhancing law enforcement through improving prescription drug monitoring programs should be associated with development of a more effective therapeutic strategy for heroin abuse.

Currently used therapeutic agents for treatment of heroin abuse and other opioid drugs of abuse include naloxone for overdose treatment and buprenorphine, methadone, and naltrexone for addiction treatment. These therapeutic agents may be used in various formulations/devices, such as nasal spray device for naloxone[6] for fast overdose treatment and extended-release naltrexone for relapse-preventing addiction treatment.[7]

All of these therapeutic agents in the current clinical use, and other therapeutic candidates under preclinical/clinical development, bind to μ-opiate receptors (and/or a related receptors) in the brain and, thus, block the physiological effects of heroin or another opioid used.

The overdose treatment with naloxone appears to be effective, but the precondition is that the naloxone treatment can begin soon enough after a heroin overdose. For the problem, once overdosed, a subject suffering from OUD may continue to get overdosed again and again until fatal. Some subjects survived from one overdose with treatment in hospital, and then died of another overdose the next day.[2] Even worse, the use of naltrexone or its extended-release formulation Vivitrol® actually increased heroin overdose.[8-10]

It has been known that heroin (3,6-diacetylmorphine, synthesized from morphine) behaves as a prodrug and its effects are mediated by its metabolites (6-MAM and morphine depicted in FIG. 1).[11,12] There are two main cholinesterases, including acetylcholinesterase (AChE) and butyrylcholinesterase (BChE). Which cholinesterase (AChE or BChE) is mainly responsible for heroin hydrolysis has been controversial. It was once proposed that human erythrocyte AChE is responsible for hydrolyzing heroin.[21] However, further studies by Lockridge et al. indicated that human serum BChE, instead of erythrocyte AChE, is responsible for hydrolyzing heroin.[13] As previously reported, catalytic parameters for BChE-catalyzed hydrolysis of heroin were inconsistent ($k_{cat}$=12.5 to 540 min$^{-1}$ and $K_M$=110 to 3500 μM).[13,22,23]

A truly effective OUD treatment should account for not only rescuing subjects who have already been overdosed, but also reducing the risk of further overdose. Furthermore, an effective treatment should be informed by a clarified understanding of the enzyme(s) responsible for opioid metabolism.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently disclosed subject matter includes methods of treating an opioid use disorder. In some embodiments, the involves administering to the subject a butyrylcholinesterase (BChE) inhibitor.

In some embodiments, the BChE inhibitor is selected from the group consisting of ethopropazine, cymserine, bisnorcymserine, phenethylnorcymserine, tacrine, pyridostigmine, physostigmine, neostigmine, rivastigmine, eptastigmine, iso-ompa, hetopropazine, bambuterol, MF-8622 or combinations thereof.

In some embodiments, the BChE inhibitor is administered at a dose of at least about 0.1, 0.2, 0.3, 0.4, 0.5, 0.6, 0.7, 0.8, 0.9, 1, 2, 3, 4, 5, 6, 7, 8, 9, or 10 mg/kg. In some embodiments, the BChE inhibitor is administered at a dose of at least about 0.1, 0.2, 0.3, 0.4, 0.5, 0.6, 0.7, 0.8, 0.9, 1, 2, 3, 4, or 5 mg/kg. In some embodiments, the BChE inhibitor is administered at a dose of less than about 10 mg/kg.

In some embodiments, the method also involves identifying the subject as having a history of opioid use. In some embodiments, the method involves identifying an indicator of opioid toxicity in the subject. In some embodiments, the method involves identifying the subject as overdosing or being at risk of overdosing.

In some embodiments, the method involves identifying the subject as desiring or being in need of opioid abstinence, reduction of opioid craving, reduction of opioid withdrawal symptoms, and/or reduction of opioid use.

In some embodiments, the method involves administering to the subject an opioid receptor antagonist. In some embodiments, the method involves identifying the subject as already receiving treatment comprising an opioid receptor antagonist. As used herein, the term "opioid receptor antagonists" refer to peptides, or small molecules that bind to mu, delta, kappa, and/or opioid receptor like-1 receptors and inhibit or reduce the binding of the native agonist to at least one opioid receptor. Examples of opioid receptor antagonists include, but are not limited to, naltrexone, naloxone, nalbuphine, butorphanol, and combinations thereof.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1:
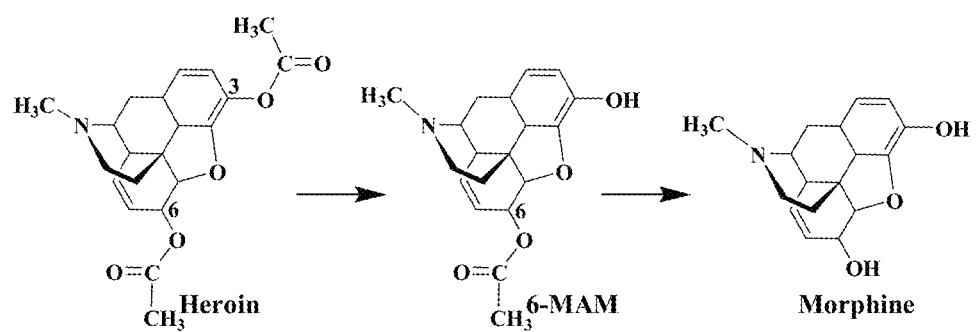
FIG. 1 shows the metabolic pathway of heroin to morphine—hydrolysis reaction catalyzed by cholinesterases.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes methods of treating an opioid use disorder.

As used herein, the terms "opiate" and "opioid" are used interchangeably to refer to compounds, or pharmaceutical formulations where at least one an ingredient acts as an agonist or partial agonist at the mu-opioid receptor. Non-limiting examples of opiates include: heroin, morphine, oxycodone, hydrocodone, hydromorphone, fentanyl, levorphanol, buprenorphine, methadone, pentazocine, codeine, meperidine, tramadol, tapentadol, and the like.

With reference to the Diagnostic and Statistical Manual for Mental Disorders, 5th Edition, American Psychiatric Association, 2013 (also referred to herein as DSM5), the disclosure of which is incorporated by reference herein in its entirety, "opioid use disorder" is characterized by signs and symptoms that reflect compulsive, prolonged self-administration of opioid substances that are used for no legitimate medical purpose or, if another medical condition is present that requires opioid treatment, they are used in doses greatly in excess of the amount needed for that medical condition.

As used herein, the term "treatment" or "treating" refers to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. Accordingly, treatment for an opioid use disorder can include, for example, treatment to produce opioid abstinence, reducing or eliminating opioid craving, reducing or eliminating opioid withdrawal symptoms, reducing or eliminating opioid use, reducing or eliminating risk of overdose, and/or reducing or eliminating risk of lethal overdose.

As used herein, the terms "eliminate," "eliminating," "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. As will be understood by those of ordinary skill in the art, when the term "prevent" or "prevention" is used in connection with a prophylactic treatment, it should not be understood as an absolute term that would preclude any modicum of pain in a subject. Rather, as used in the context of prophylactic treatment, the term "prevent" can refer to inhibiting the development of or limiting the severity of, arresting the development of pain, and the like.

As used herein, the terms "opiate related overdose" or "opiate overdose" refer to the condition wherein a subject consumes, via any route of administration, a substance containing at least one opiate to where the opiate concentration exceeds the therapeutic concentration and leads to opiate toxicity. Opiates need not be abused to cause overdoses. Opiate toxicity indicators include symptoms of central nervous system depression. Symptoms of opiate toxicity may include: loss of consciousness, unresponsiveness to outside stimulus, wakefulness with an inability to talk, abnormal breathing patterns (slow, shallow, erratic, or cessation thereof), shifting skin tone (to either blue or grey), choking sounds, vomiting, body limpness, pale or clammy skin, and abnormal heartbeat (slow, erratic, absent).

Embodiments of the methods described herein include administering to a subject in need of treatment for an opioid use disorder an effective amount of a butyrylcholinesterase (BChE) inhibitor.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "subject" refers to a target of administration. The subject of the herein disclosed methods can be a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A "patient" refers to a subject afflicted with a disease or disorder. The term "patient" includes human and veterinary subjects.

As used herein, the term "butyrylcholinesterase inhibitor" refers to inhibitors of the butyrylcholinesterase enzyme. In some embodiments, the butyrylcholinesterase inhibitor is either specific or selective for butyrylcholinesterase. As used herein, an inhibitor is a specific or selective BChE inhibitor when it is more highly selective for BChE over acetylcholinesterase (AChE). In some embodiments, the selective BChE inhibitor has minimal inhibitory activity toward AChE. In some embodiments, the selective BChE inhibitor has about 10, 100, or 1000-fold selectivity for BChE over AChE, as measured by $IC_{50}$. Examples of certain BChE inhibitors are referred to in Giacobini et al. which is incorporated herein by reference. Examples of BChE inhibitors include, but are not limited to, ethopropazine, cymserine, bisnorcymserine, phenethylnorcymserine, tacrine, pyridostigmine, physostigmine, neostigmine, rivastigmine, eptastigmine, iso-ompa, hetopropazine, bambuterol, MF-8622 or combinations thereof.

The term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level if or any particular patient will depend upon a variety of factors including the disorder being treated and the severity of the disorder; the specific composition employed; the age, bodyweight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products.

In some embodiments of the presently-disclosed subject matter, the method of treating opioid use disorder in a subject in need thereof involves administering to the subject a selective butyrylcholinesterase (BChE) inhibitor.

In some embodiments, the BChE inhibitor is selected from the group consisting of ethopropazine, cymserine, bisnorcymserine, phenethylnorcymserine, tacrine, pyridostigmine, physostigmine, neostigmine, rivastigmine, eptastigmine, iso-ompa, hetopropazine, bambuterol, MF-8622 or combinations thereof.

In some embodiments, the BChE inhibitor is administered at a dose of at least about 0.1, 0.2, 0.3, 0.4, 0.5, 0.6, 0.7, 0.8, 0.9, 1, 2, 3, 4, 5, 6, 7, 8, 9, or 10 mg/kg. In some embodiments, the BChE inhibitor is administered at a dose of at least about 0.1, 0.2, 0.3, 0.4, 0.5, 0.6, 0.7, 0.8, 0.9, 1, 2, 3, 4, or 5 mg/kg. In some embodiments, the BChE inhibitor is administered at a dose of less than about 10 mg/kg.

In some embodiments, the method also involves identifying the subject as having a history of opioid use.

In some embodiments, the method involves identifying an indicator of opioid toxicity in the subject.

In some embodiments, the method involves identifying the subject as overdosing or being at risk of overdosing.

In some embodiments, the method involves identifying the subject as desiring or being in need of opioid abstinence, reduction of opioid craving, reduction of opioid withdrawal symptoms, and/or reduction of opioid use.

In some embodiments, the method involves administering to the subject an opioid receptor antagonist. In some embodiments, the method involves identifying the subject as already receiving treatment comprising an opioid receptor antagonist. As used herein, the term "opioid receptor antagonists" refer to peptides, or small molecules that bind to mu, delta, kappa, and/or opioid receptor like-1 receptors and inhibit or reduce the binding of the native agonist to at least one opioid receptor. Examples of opioid receptor antagonists include, but are not limited to, naltrexone, naloxone, nalbuphine, butorphanol, and combinations thereof.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, in some embodiments ±0.01%, and in some embodiments ±0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting examples. The following examples may include compilations of data that are representative of data gathered at various times during the course of development and experimentation related to the present invention.

EXAMPLES

Example 1. BChE and Opioid Compounds

The purified recombinant human BChE protein was prepared as in a previous study.[27] Briefly, the BChE protein was expressed in CHO—S cells, and the secreted enzyme in the culture medium was purified by a two-step approach, including ion exchange chromatography using QFF anion exchanger and affinity chromatography using procainamide-sepharose. The purified protein was stored at −80° C. before the use. Heroin and its metabolite 6-MAM were provided by the National Institute on Drug Abuse (NIDA) Drug Supply Program (Bethesda, Md.). All other supplies (including ethopropazine and naltrexone) were purchased from Sigma-Aldrich (St. Louis, Mo.).

Example 2. Animal Studies

Male CD-1 mice (28-32 g) were ordered from Harlan (Harlan, Indianapolis, Ind.), and housed in cage. All mice were allowed ad libitum access to food and water and maintained on a 12 h light/12 h dark cycle, with the lights on at 8:00 a.m. at a room temperature of 21-22° C. Experiments were performed in a same colony room in accordance with the Guide for the Care and Use of Laboratory Animals as adopted and promulgated by the National Institutes of Health. The animal protocol was approved by the IACUC (Institutional Animal Care and Use Committee) at the University of Kentucky.

Example 3. Enzyme Activity Assay

An in vitro enzyme activity assay was used to assess BChE activity. For kinetic analysis of the catalytic activity of BChE against heroin, the purified enzyme and heroin were incubated in 0.1 M phosphate buffer, pH 7.4, at 37° C. The enzymatic reaction was terminated and the protein was precipitated by adding 100 μl of iced 50% acetonitrile/0.5 M hydrochloric acid, followed by 5 min centrifugation at 15,000 g. The resulting supernatant was subjected to reverse-phase HPLC (RP-HPLC) on a 5 μm C18 110 Å column (250×4.6 mm; Gemini) and RP-HPLC was performed using the mobile phase consisting of 20% acetonitrile in 0.1% TFA. The remaining substrate (heroin) and the formed reaction product (6-MAM) were monitored by a fluorescence detector with an excitation wavelength of 230 nm and emission wavelength of 315 nm and by monitoring UV absorbance at 230 nm. The quantification was based on a standard curve prepared using an authentic standard compound. The measurement was performed in triplicate, and the catalytic parameters were determined by using the Michaelis-Menten kinetic equation.

Example 4. Locomoter Activity Assay

To determine the effects of ethopropazine on heroin-induced hyperactivity, locomotor activity tests were performed in high density, non-porous plastic chambers measuring 50 cm (L)×50 cm (W)×38 cm (H) in a light- and sound-attenuating behavioral test enclosure (San Diego Instruments, San Diego, Calif.). This system can test 8 mice at the same time. Cumulative distance traveled and speed were recorded by EthoVision XT video tracking system (Noldus Information Technology, Wageningen, Netherlands) to represent the locomotor activity. Mice were introduced to the test chambers for one habituation session (no injection). Before the test session, mice were allowed to acclimate to the test chambers for at least 60 minutes, and the total distance traveled during this period of time were determine the basal activity. Then, ethopropazine or saline (negative control) was administered through intravenous (IV) injection. At 10 min after the ethopropazine or saline injection, the mice were given a pharmacological dose of heroin (e.g., 2.5 or 5 mg/kg, IP). After the heroin administration, mice were immediately returned to the test chamber for a 60-minute session of activity monitoring.

Example 5. Protection Studies

Heroin-induced acute toxicity was characterized in this study by the occurrence of death. A protection experiment was performed by pretreatment of mice with ethopropazine (10 mg/kg, IV) 10 min before administration of heroin (25 mg/kg, IV). Following the heroin administration, mice were immediately placed in containers for observation. The presence or absence of death was recorded for 6 hours following heroin administration.

Example 6. Catalytic Parameters of the Primary Enzyme Involved in Heroin Activation Once administered, heroin is very rapidly metabolized by cholinesterases to 6-monoacetylmorphine (6-MAM) first, and then to morphine (see FIG. 1). Both 6-MAM and morphine are responsible for the toxic and physiological effects of heroin.[13-20] In fact, heroin is at least 10-fold more toxic than morphine,[16] but the binding affinity of heroin itself with the μ-opiate receptors is significantly lower than that of morphine. The most toxic metabolite is 6-monoacetylmorphine (6-MAM) which has the highest binding affinity with the μ-opiate receptors. 6-MAM (with a relatively shorter biological half-life compared to morphine) is mainly responsible for the acute toxicity,[17] whereas morphine (with a much longer biological half-life) is mainly responsible for the long-term toxicity, of heroin. So, cholinesterases are crucial enzymes that control the metabolic profile, and thus affect the toxic and physiological effects, of heroin.

Figure 2A:
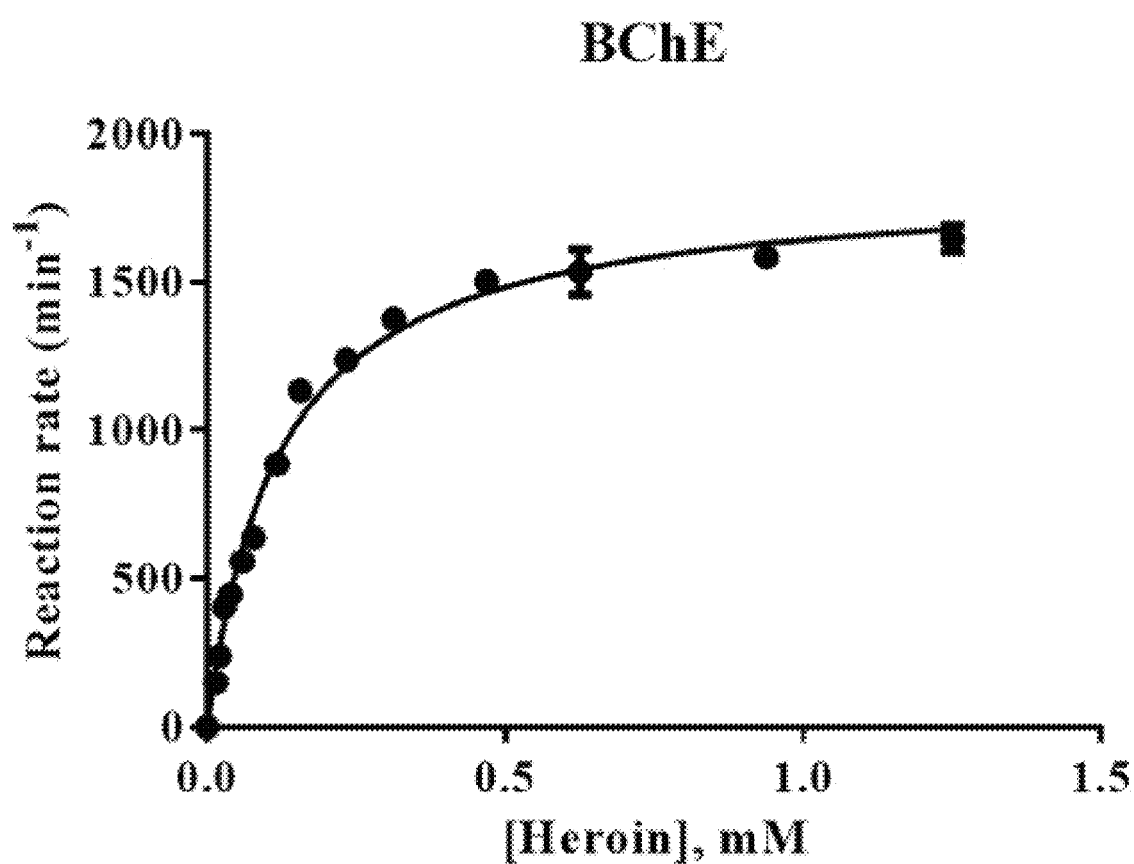
FIG. 2A shows Plot of measured initial reaction rates (represented in nM min$^{-1}$ per nM enzyme, or min$^{-1}$, at 37° C., measured in triplicate, with error bars in standard deviations) versus the substrate (heroin) concentration for recombinant human BChE-catalyzed hydrolysis of heroin.

The Michaelis-Menten kinetic analysis of the BChE-catalyzed hydrolysis of heroin was performed at 37° C. The kinetic data (FIG. 2A) reveal that recombinant human BChE is highly efficient for heroin hydrolysis (kcat=1840 min$^{-1}$ and KM=120 μM), which is qualitatively consistent with the conclusion obtained by Lockridge et al.[13] According to reported pharmacokinetic studies,[17] heroin is converted to 6-MAM with a very high metabolic rate in blood (with a rate constant for heroin hydrolysis to 6-MAM as high as 12.092 min$^{-1}$), and the estimated metabolic rate of heroin in brain was much lower. The very different metabolic rates for heroin in blood and brain calculated by the model were confirmed by in vitro experiments,[18] which also supports the notion that BChE (which is the dominant cholinesterase in serum) is the primary enzyme responsible for heroin activation. Further, heroin is either eliminated very rapidly from the body (by some direct pathway, e.g. urine) or metabolized rapidly to 6-MAM in plasma, according to the well-established pharmacokinetic (PK) model (the rate constant is 13.757 min$^{-1}$ for direct heroin elimination and 12.092 min$^{-1}$ for heroin hydrolysis to 6-MAM).[18] When the metabolic pathway of heroin by BChE is blocked, heroin will mainly go through the direct elimination process to urine. Hence, blocking BChE-catalyzed hydrolysis of heroin should help to significantly attenuate the actual toxicity and physiological effects of heroin.

Example 7. Effects of Ethopropazine on Heroin-Induced Hyperactivity

Figure 2B:
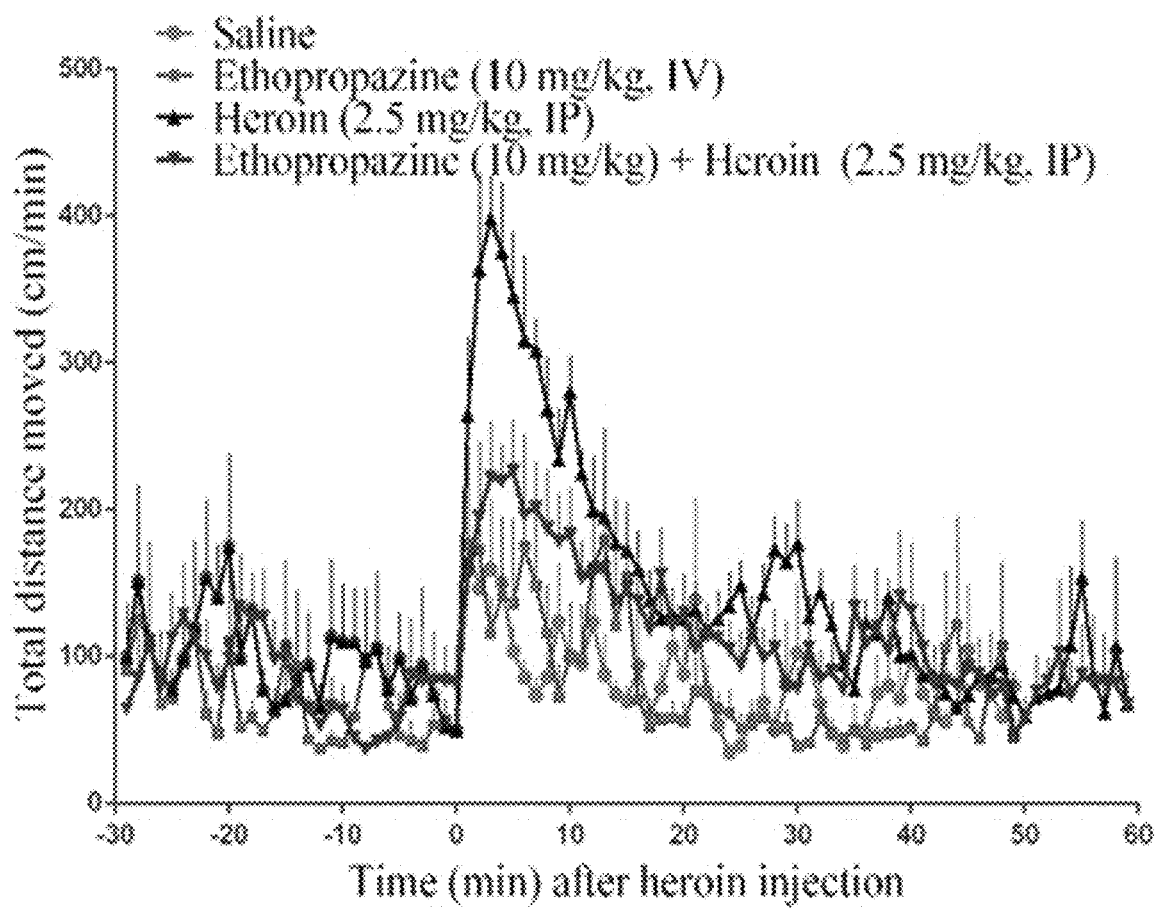
FIG. 2B shows Locomotor activity in mice expressed as total distance traveled (in centimeters) per min after heroin injection (2.5 mg/kg, IP) or saline, with or without ethopropazine injection (10 mg/kg, IV) 10 min prior to the heroin (or nothing) injection (2.5 mg/kg, IP) at the time 0. A group of eight mice (n=8) were used at the same time for each dose condition.

Notably, many cholinesterase inhibitors have been approved by the FDA as therapeutic agents for treatment of Alzheimer's disease (AD), myasthenia gravis, glaucoma, and Parkinson's disease etc. Most of these cholinesterase inhibitors are able to inhibit both AChE and BChE, without the desirable high selectivity for BChE over AChE. Nevertheless, ethopropazine (a BChE inhibitor approved by the FDA for treatment of Parkinson's disease) is highly selective for BChE over AChE, with $IC_{50}$=210-300 nM for BChE and $IC_{50}$=210 μM for AChE (~1000-fold selectivity).[24] So, ethopropazine was used to examine whether a BChE-selective inhibitor can really attenuate the toxic and physiological effects of heroin in mice. The effects of ethopropazine on heroin-induced hyperactivity was determined by performing locomotor activity tests in high density, non-porous plastic chambers measuring 50 cm (L)×50 cm (W)×38 cm (H) in a light- and sound-attenuating behavioral test enclosure (San Diego Instruments, San Diego, Calif.). As seen in FIG. 2B, ethopropazine (10 mg/kg, IV) administration 10 min prior to the heroin (2.5 mg/kg, IP) injection significantly attenuated heroin-induced hyperactivity.

Example 8. Effects of Ethopropazine on Heroin-Induced Acute Toxicity

Ethopropazine was tested further for its effectiveness in protecting mice against heroin-induced acute toxicity. Heroin-induced acute toxicity was characterized by the lethality (occurrence of death). For the protection experiments, a single dose of ethopropazine was administrated (IV) prior to administration of a lethal dose ($LD_{100}$) of heroin (e.g. 25 mg/kg, IV). At 10 min after IV administration of ethopropazine or saline (negative control), the mice were given a lethal dose ($LD_{100}$) of heroin. The protection experiments were performed under various dose conditions (n=6 for each scenario). Depicted in FIG. 3 are the data obtained from the protection experiments with ethopropazine (1 or 10 mg/kg, IV) and/or naltrexone (0.3 mg/kg, IV); a higher dose (1 mg/kg, IV) of naltrexone was used and it was noted that the IV dose of 1 mg/kg would be too high because the mice injected intravenously with 1 mg/kg naltrexone were not able to stand and could hardly move at all.

Figure 3:
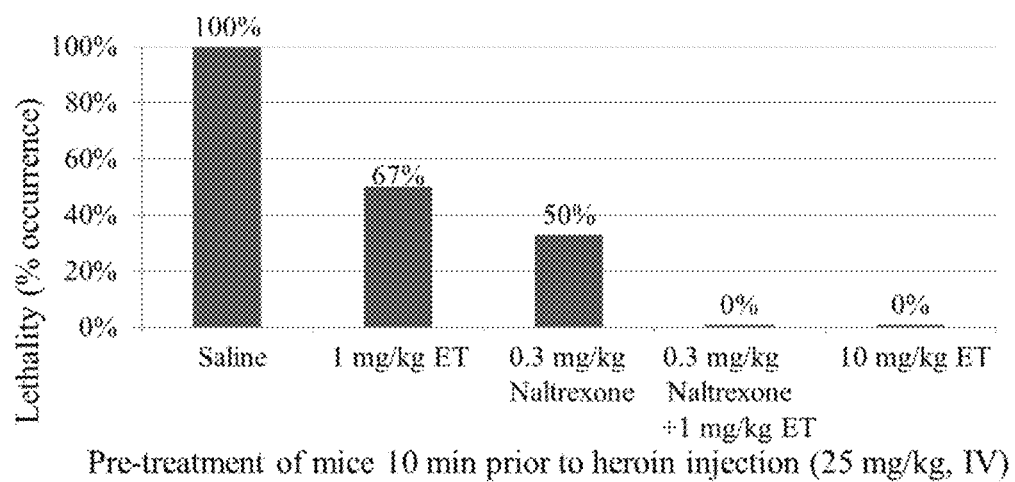
FIG. 3 shows Effectiveness of ethopropazine (ET) and naltrexone in protection of mice against the acute toxicity of a lethal dose of heroin (25 mg/kg, IV). ET and/or naltrexone (IV) was administered (IV) 10 min before the heroin administration, in comparison with the control group (saline) without ET or naltrexone administration. Each data point represents the percentage of mice (n=6 for each dose condition) exhibiting heroin-induced lethality.

The data depicted in FIG. 3 reveal that, without ethopropazine or naltrexone administration, all mice died within 2 min after the heroin injection (25 mg/kg, IV). However, pre-treatment of mice with ethopropazine (10 mg/kg, IV) 10 min before the heroin injection protected all mice against the acute toxicity of a lethal dose of heroin (25 mg/kg, IV). So, 10 mg/kg ethopropazine was able to protect all of the mice from the heroin-induced lethality (full protection).

It was also tested whether Galantamine (a highly potent and selective inhibitor of AChE, approved by the FDA for treatment of Alzheimer's disease) can also attenuate heroin-induced toxicity, and found that pre-treatment of mice with Galantamine at a dose of 10 or 5 mg/kg (IV or IP) before the heroin injection did not protect any mouse against the acute toxicity of a lethal dose of heroin (25 mg/kg, IV), which is consistent with the concept that BChE, rather than AChE, is the primary heroin-activating enzyme.

Additional data in FIG. 3 indicate that 1 mg/kg ethopropazine or 0.3 mg/kg naltrexone only provided partial protection, but the combined use of 0.3 mg/kg naltrexone and 1 mg/kg ethopropazine provided the full protection. So, the protection effects of ethopropazine and naltrexone are indeed cooperative, as expected.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Drash, W. & Blau, M. CNN Front Page News—In America's drug death capital: How heroin is scarring the next generation (www.cnn.com/2016/09/16/health/huntington-heroin/index.html). 5:45 PM ET, Fri., Sep. 16, 2016 (last seen: December 2017).
2. USDOJ. CD No. 2 ("1. Chasing the Dragon; 2. Heroin Hurts; 3. Heroin is Hell; 4. Heroin is Here; 5 Heroin's Hold"), distributed to the invited attendees of US Attorney-General Loretta E. Lynch's "National Heroin & Opioid Awareness Week" policy speech at College of Pharmacy, University of Kentucky on Sep. 20, 2016. (2016).
3. ONDCP. Prescription Drug Monitoring Programs (obamawhitehouse.archives.gov/sites/default/files/ondcp/Fact_Sheets/pdmp_fact_sheet_4-8-11.pdf). April 2011 (last seen: December 2017) (2011).
4. WLKY. Study shows prescription drug abuse declining in Kentucky (www.wlky.com/news/study-shows-prescription-drug-abuse-declining-in-kentucky/34380884) and the comments on the report. 4:31 PM EDT Jul. 27, 2015 (last seen: December 2017) (2015).
5. USDOJ. CD No. 1 ("CD of Heroin Facts and Other Documents"), distributed to the invited attendees of US Attorney-General Loretta E. Lynch's "National Heroin & Opioid Awareness Week" policy speech at College of Pharmacy, University of Kentucky on Sep. 20, 2016. (2016).
6. Krieter, P. et al. Pharmacokinetic Properties and Human Use Characteristics of an FDA-Approved Intranasal Naloxone Product for the Treatment of Opioid Overdose. J. Clin. Pharmacol. 56, 1243-1253 (2016).
7. Zaaijer, E. R., Goudriaan, A. E., Koeter, M. W., Booij, J. & van den Brink, W. Acceptability of Extended-Release Naltrexone by Heroin-Dependent Patients and Addiction Treatment Providers in the Netherlands. Subst. Use Misuse 51, 1905-1911 (2016).
8. Ritter, A. J. Naltrexone in the treatment of heroin dependence: relationship with depression and risk of overdose. Australian and New Zealand Journal of Psychiatry 36, 224-228 (2002).
9. SAMHSA. The Facts about Naltrexone for Treatment of Opioid Addiction (store.samhsa.gov/shin/content//SMA12-4444/SMA12-4444.pdf), HHS Publication No. (SMA) I2-4444. (2012).
10. Gibson, A. & Degenhardt, L. Mortality related to naltrexone in the treatment of opioid dependence: A comparative analysis (ndarc.med.unsw.edu.au/resource/mortality-related-naltrexone-treatment-opioid-dependence-comparative-analysis). NDARC Technical Report No. 229 (2005).
11. Inturrisi, C. E. et al. Evidence from opiate binding studies that heroin acts through its metabolites. Life Sci. 33(Suppl. 1), 773-776 (1983).
12. Strandberg, J. J. et al. Toxicological analysis in rats subjected to heroin and morphine overdose. Toxicol. Lett. 166, 11-18 (2006).
13. Lockridge, O., Mattershaw-Jackson, N., Eckerson, H. W. & LaDu, B. N. Hydrolysis of diacetylmorphine (heroin) by human serum cholinesterase. J. Pharmacol. Exp. Ther. 215, 1-8 (1980).
14. Eddy, N. B. & Howes, H. A. Studies of morphine, codeine and their derivatives VIII Monoacetyl- and diacetylmorphine their hydrogenated derivatives. J. Pharmacol. Exp. Ther. 53, 430-439 (1935).
15. Wright, C. I. & Barbour, F. A. The respiratory effects of morphine, codeine and related substances IV. The effect of alpha-monoacetylmorphine, monoacetyldihydromorphine, diacetylmorphine (heroin) and diacetyldihydromorphine on the respiratory activity of the rabbit. J. Pharmacol. Exp. Ther. 54, 25-33 (1935).
16. Selley, D. E. et al. mu-Opioid receptor-mediated G-protein activation by heroin metabolites: evidence for greater efficacy of 6-monoacetylmorphine compared with morphine. Biochem. Pharmacol. 62, 447-455 (2001).
17. Andersen, J. M., Ripel, A., Boix, F., Normann, P. T. & Morland, J. Increased locomotor activity induced by heroin in mice: pharmacokinetic demonstration of heroin acting as a pro-drug for the mediator, 6-monoacetylmorphine, in vivo. J. Pharmacol. Exp. Ther. 331, 153-161 (2009).
18. Boix, F., Andersen, J. M. & Morland, J. Pharmacokinetic modeling of subcutaneous heroin and its metabolites in blood and brain of mice. Addict. Biol. 18, 1-7 (2013).
19. NIDA. DrugFacts: Heroin (www.drugabuse.gov/publications/drugfacts/heroin). (2015).
20. Wikipedia. en.wikipedia.org/wiki/Morphine#cite note-urlDrugFacts:_Heroin_.7C_National_Institute_on_Drug_Abuse_.28NIDA.29-23 (last seen: Mar. 6, 2018). (2018).
21. Smith, D. A. & Cole, W. J. Identification of an arylesterase as the enzyme hydrolysing diacetylmorphine (heroin) in human plasma. Biochem. Pharmacol. 25, 367-370 (1976).
22. Salmon, A. Y., Goren, Z., Avissar, Y. & Soreq, H. Human erythrocyte but not brain acetylcholinesterase hydrolyses heroin to morphine. Clinical and Experimental Pharmacology and Physiology 26, 596-600 (1999).

23. Kamendulis, L. M., Brzezinski, M. R., Pindel, E. V., Bosron, W. F. & Dean, R. A. Metabolism of cocaine and heroin is catalyzed by the same human liver carboxylesterases. *Journal of Pharmacology and Experimental Therapeutics* 279, 713-717 (1996).
24. Atack, O. A., Vu, Q.-S., Soncrant, T. T., Brossi, A. & Rapoport, S. I. Comparative Inhibitory Effects of Various Physostigmine Analogs against Acetyl- and Butyryicholinesterases. *J. Pharm. Exp. Therap.* 249, 194-202 (1989).
25. Bliss, C. I. The calculation of microbial assays. *Bacteriol. Rev.* 20, 243-258 (1956).
26. Bliss, C. I. The toxicity of poisons applied jointly. *Ann. Appl. Biol.* 26, 585-615 (1939).
27. Chen, X. et al. Kinetic characterization of a cocaine hydrolase engineered from mouse butyrylcholinesterase. *Biochem. J.* 466, 243-251 (2015).
28. Giacobini, Ezio. Selective Inhibitors of Butyrylcholinesterase: A valid alternative for therapy of Alzheimer's Disease? *Drug Aging.* 18(12) 891-898 (2001).

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of reducing or eliminating risk of lethal overdose in a subject overdosing or being at risk of overdosing from heroin administration, comprising: administering to the subject an effective amount of a selective butyrylcholinesterase (BChE) inhibitor.

2. The method of claim 1, and further comprising identifying the subject as having a history of opioid use.

3. The method of claim 1, wherein the BChE inhibitor is selected from the group consisting of ethopropazine, cymserine, bisnorcymserine, phenethylnorcymserine, tacrine, pyridostigmine, physostigmine, neostigmine, rivastigmine, eptastigmine, iso-ompa, hetopropazine, bambuterol, MF-8622 or combinations thereof.

4. The method of claim 1, wherein the BChE inhibitor is administered intravenously, intranasally, intramuscularly, intraperitoneally, or intraocularly.

5. The method of claim 1, and further comprising administering to the subject an opioid receptor antagonist.

6. The method of claim 1, and further comprising identifying the subject as receiving treatment comprising an opioid receptor antagonist.

7. The method of claim 6, wherein the opioid receptor antagonist is selected from the group consisting of naltrexone, naloxone, nalbuphine, butorphanol, and combinations thereof.

8. The method of claim 6, wherein the opioid receptor antagonist is naltrexone.

9. The method of claim 1, and further comprising identifying an indicator of opioid toxicity in the subject.

10. The method of claim 9, and further comprising administering to the subject an opioid receptor antagonist.

11. The method of claim 1, and further comprising identifying the subject as overdosing or being at risk of overdosing.

12. The method of claim 11, wherein the BChE inhibitor is administered at a dose of at least about 0.1 mg/kg.

13. The method of claim 12, and further comprising administering to the subject an opioid receptor antagonist.

14. The method of claim 1, and further comprising identifying the subject as desiring or being in need of opioid abstinence, reduction of opioid craving, reduction of opioid withdrawal symptoms, and/or reduction of opioid use.

15. The method of claim 1, and further comprising administering to the subject an opioid receptor antagonist or identifying the subject as receiving treatment comprising an opioid receptor antagonist.

16. The method of claim 15, wherein the opioid receptor antagonist is selected from the group consisting of naltrexone, naloxone, nalbuphine, butorphanol, and combinations thereof.

17. The method of claim 15, wherein the opioid receptor antagonist is naltrexone.

18. The method of claim 15, and further comprising identifying the subject as being at risk of overdosing.

19. The method of claim 18, wherein the BChE inhibitor is administered at a dose of at least about 0.1 mg/kg.

20. The method of claim 15, wherein the BChE inhibitor is administered at a dose of at least about 0.1 mg/kg.

* * * * *